(12) United States Patent
Davis

(10) Patent No.: US 6,258,253 B1
(45) Date of Patent: Jul. 10, 2001

(54) VAPOR CORROSION CELL AND METHOD OF USING SAME

(75) Inventor: Dennis D. Davis, Las Cruces, NM (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 0 days.

(21) Appl. No.: 09/292,237

(22) Filed: Apr. 15, 1999

(51) Int. Cl.$^7$ ........................................ G01N 27/26
(52) U.S. Cl. .................... 205/776; 204/400; 204/404; 204/280; 205/775.5
(58) Field of Search ................... 204/404, 400; 205/775.5, 776, 776.5, 777

(56) References Cited

U.S. PATENT DOCUMENTS

| | | |
|---|---|---|
| 3,954,590 * | 5/1976 | Czuha ........................... 204/430 |
| 4,049,525 | 9/1977 | Dutton et al. . |
| 4,587,479 | 5/1986 | Rhoades et al. . |
| 4,752,360 | 6/1988 | Jasinski . |
| 4,994,159 * | 2/1991 | Agarwala et al. ................. 204/404 |
| 5,015,355 | 5/1991 | Schiessl . |
| 5,188,715 * | 2/1993 | Chen et al. ....................... 205/777 |
| 5,208,162 | 5/1993 | Osborne et al. . |
| 5,290,407 * | 3/1994 | Syrett et al. ...................... 205/734 |
| 5,310,470 * | 5/1994 | Agarwala et al. ................. 204/404 |
| 5,411,890 | 5/1995 | Falat . |
| 5,481,198 | 1/1996 | Patel . |
| 5,529,668 | 6/1996 | Hall . |
| 5,531,103 | 7/1996 | Eaton . |
| 5,639,959 | 6/1997 | Reiber . |
| 5,712,559 | 1/1998 | Moore et al. . |

* cited by examiner

Primary Examiner—T. Tung
(74) Attorney, Agent, or Firm—James M. Cate

(57) ABSTRACT

The present invention provides a vapor corrosion cell for a real-time and quantitative measurement of corrosion of conductive materials in atmospheres containing chemically reactive gases and water vapor. Two prototypes are provided. Also provided are various applications of this apparatus in industry.

13 Claims, 3 Drawing Sheets

VAPOR CORROSION CELL AND METHOD OF USING SAME

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates generally to the field of electrochemistry. More specifically, the present invention relates to a real-time, quantitative electrochemical device for the measurement of corrosion of conductive materials in atmospheres containing chemically reactive gases and water vapor.

2. Description of the Related Art

Many metal-containing devices and structures must function in corrosive atmospheres which cause them to deteriorate over time. Corrosion may take the form of metal oxides resulting from reaction with oxygen in the air, or corrosion may form by compounds formed with the effluent of industrial processes, such as hydrogen sulfide.

A common method of measuring corrosion employs resistance measurement of a metallic corrodible test element to indicate, by change in electrical resistance, the amount of metal that has been lost by corrosion over a period of time. There are several corrosive probes, sensors or processes currently available for evaluating corrosive environments by measuring an electric current passed through the corrosive media itself.

U.S. Pat. No. 4,752,360 to Jasinski discloses a corrosion probe having sandwich of electrodes and dielectric layers for measuring the corrosion rates of metals in corrosive environment. In one application, the probe must be immersed in a liquid corrosive media, including corrosive elements such as carbon dioxide or hydrogen sulfide in a brine solution used in oil drilling. Current is conducted through the conductive elements and directly through the liquid brine. U.S. Pat. No. 4,049,525 to Dutton is related to a corrosion test cell having a plurality of conductive elements connectable to test electrodes, wherein the electrodes extend into a corrosive liquid environment during operation. The corrosion measuring cell of Schiessl, U.S. Pat. No. 5,015,355, includes a plurality of electrodes which are embedded in a solid (concrete) media for sensing the occurrence of corrosion of steel bars by sensing variations in current flow between the electrodes. The sensed current is again a current flowing through the corrosive media.

The prior art is deficient in the lack of a real-time, quantitative electrochemical device for measuring corrosive potential in a gaseous environment. The present invention fulfills this long-standing need and desire in the art.

SUMMARY OF THE INVENTION

The present invention is directed to a real-time, quantitative electrochemical device for the measurement of corrosion of conductive materials in a gaseous environment containing chemically reactive gases and water vapor. This device is called a vapor corrosion cell herein. This vapor corrosion cell contains strips of alternating dissimilar conducting materials, usually metals or alloys, such as Ti and Al strips, separated by a thin strip of non-conducting material in a sandwich structure. All the strips of each similar conducting material are electrically connected. The edges of the strips are exposed to the atmosphere containing water vapor and a reactive vapor or gas. Under these conditions, an electrochemical potential is developed between dissimilar metals and if the electrical circuit is closed, a current flows. Measurement of the current indicates electrochemical activity and thus the corrosion occurring at the exposed surfaces.

In one embodiment of the present invention, there is provided an apparatus for measuring corrosion in an environment, the apparatus comprising a series of strips of a first conducting material ($M_1$) alternated by a series of strips of a second conducting material ($M_2$), separated by a thin strip of non-conducting material in a sandwich structure. All of the strips of each similar conducting material are electrically connected. The cell, having the dimension as small as 50 mm×50 mm×10 mm (length×width×depth), is further connected to a current measuring/recording device, such as an ammeter. The resulting apparatus provides a real-time and quantitative measurement of corrosion. Preferably, the non-conducting separating strip is selected to be as thin as 0.025 mm. More preferably, from about 4 to about 10 strips of $M_1$ and an equal number of strips of $M_2$ are used.

In one embodiment, the environment contains chemically reactive gases and/or water vapor. Examples of reactive gases are carbon dioxide, nitrogen dioxide, sulfur dioxide, hydrogen halides, ammonia, hydrogen sulfide and other nitrogen-containing acids.

In another embodiment, the conducting materials are usually metals or alloys, such as aluminum, zinc, titanium, copper, etc. $M_1$ can be an active sacrificial material, while $M_2$ can be a test or reference material.

In another embodiment of the present invention, there is provided an apparatus for measuring corrosion in an environment, comprising interleaved combs of dissimilar conducting materials deposited on a non-conducting surface, such as a glass surface.

In yet another embodiment of the present invention, there is provided a method of measuring corrosion in an environment by exposing the apparatus to the environment and measuring the current and potential characteristics of the apparatus, wherein the measurement indicates electrochemical activity and thus the corrosion occurring.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
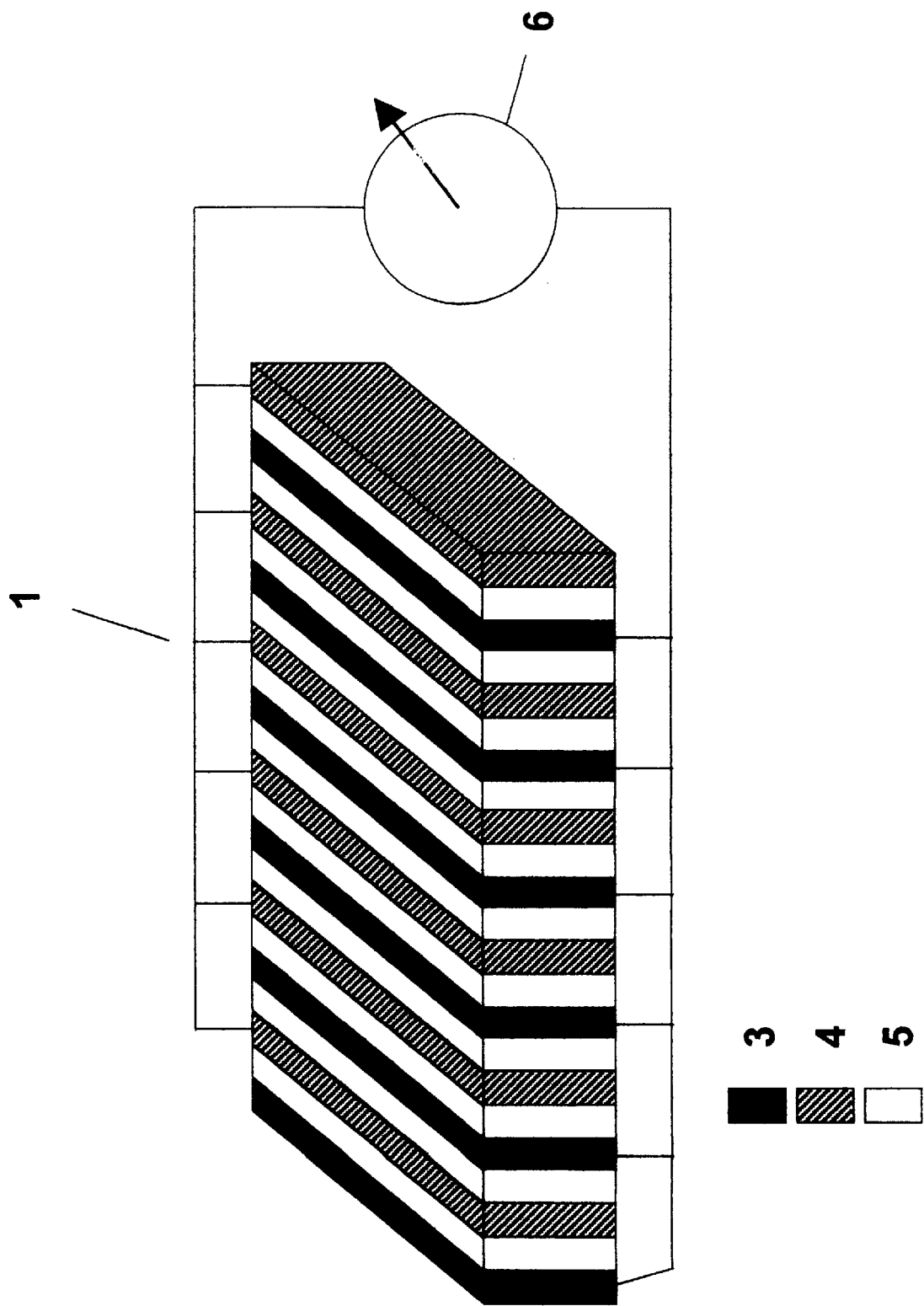
FIG. 1 shows a prototype of a vapor corrosion cell 1 comprising titanium strips 3 (or strips made of a reference metal material), aluminum strips 4 (or strips made of a sacrificial metal material) and insulating strips 5. All of the strips of each similar conducting material are electrically connected. The cell is molded into a compact block and further connected to a current measuring/recording device 6, such as an ammeter.

The present invention relates to methods and apparatus for sensing and evaluating the corrosive effects of atmospheric and chemical substances. The need for such an apparatus relates to the necessity in industry to monitor closely the effects of corrosive environments in a real-time manner for the control and prevention of corrosion and for the monitoring of atmospheric conditions.

A sensing apparatus 1 comprises a sandwich of strips of alternating, dissimilar conducting materials 3 and 4, each separated by a thin strip of non-conducting material 5. Electrical connections are made between the sensor structure and monitoring circuitry for evaluating, recording, and transmitting data relating to the sensor's output over time. The sensing apparatus is positioned in the atmosphere to be evaluated, and the edges of the strips are exposed to atmospheres containing water vapor and a reactive substance. A low level current is conducted across the sandwich of strips, and the resulting electrical characteristics are measured, providing an indication of electrochemical activity and permitting an evaluation of the corrosion occurring at the exposed surface, and on any adjacent structures which are subject to corrosion from the atmospheric conditions.

Reactive vapors containing carbon dioxide, nitrogen dioxide, sulfir dioxide, hydrogen halides, ammonia, or other materials will react with adsorbed water on the strips, resulting in an ionic solution, forming a thin film of adsorbed solution across the non-conducting strips and permitting evaluation of the corrosive potential based on variables such as the pressure of the reactive vapors, water vapor concentration, nature of the dissimilar conductors, the nature and thickness of the nonconducting material, and the ambient temperature.

Commercial applications of the apparatus include monitoring of corrosive effects of environment such as marine environments, atmospheres in or near chemical plants, and the like, including the monitoring of air pollutants such as nitrogen and sulfur oxides, the measurement of corrosivity of polluted atmospheres surrounding exposed metal structures, and use in testing facilities for evaluating the relative resistance to corrosion of several candidate materials. Possible future operational uses of the apparatus also include real-time measuring of corrosion around space shuttle launch platforms and predicting life of the equipments.

The following terms shall have the definitions set below.

As used herein, "vapor corrosion cell" shall refer to an apparatus which contains strips of alternating dissimilar conducting materials, separated by a thin strip of non-conducting material in a sandwich structure. All the strips of each similar conducting material are electrically connected. The edges of the strips are exposed to the atmosphere containing water vapor and a reactive vapor or gas. Under these conditions, an electrochemical potential is developed between dissimilar metals and if the electrical circuit is closed, a current flows. Measurement of the current indicates electrochemical activity and thus the corrosion occurring at the exposed surfaces.

As used herein, "sandwich structure" shall refer to alternating layers of conducting and non-conducting materials fabricated into a single unit.

As used herein, "real-time measurement" shall refer to an quantitative indication of change concurrent with the action being observed.

As used herein, "reactive vapor" shall refer to a gaseous chemical species which reacts with water to form an electrically conducting solution.

As used herein, "conducting strips" shall refer to specimens of electrically conductive materials.

As used herein, "non-conducting strips" shall refer to specimens of electrically non-conducting materials or insulators.

As used here, "dissimilar conductor" shall refer to conductors with different electrochemical oxidation potentials.

As used herein, "active sacrificial material" shall refer to a metal or alloy which is easily oxidized (such as aluminum, zinc or magnesium).

As used herein, "reference material" shall refer to a metal or alloy which is difficultly oxidized (such as titanium, platinum or gold).

In one embodiment of the present invention, there is provided an apparatus for measuring corrosion in an environment, comprising a series of strips of a first conducting material ($M_1$) alternated by a series of strips of a second conducting material ($M_2$), separated by a thin strip of non-conducting material in a sandwich structure. All of the strips of each similar conducting material are electrically connected. The cell, having the dimension as small as 50 mm×50 mm×10 mm (length×width×depth), is further connected a current measuring/recording device, such as an ammeter. The resulting apparatus provides real-time and quantitative corrosion measuring. The thickness of the respective non-conductive separating strip is from about 0.01 mm to about 0.05 mm, and preferably, the non-conductive strip are as thin as 0.025 mm. More preferably, from about 4 to about 10 strips of $M_1$ and an equal number of strips of $M_2$ are used.

In one embodiment, the environment contains chemically reactive gases and/or water vapor. Examples of reactive gases are carbon dioxide, nitrogen dioxide, sulfur dioxide, hydrogen halides, ammonia, hydrogen sulfide and other nitrogen containing acids.

In another embodiment of the device of the present invention, the conducting materials used are metals or alloys, such as aluminum, zinc, titanium, copper, etc. $M_1$ can be an active sacrificial material, while $M_2$ can be a test or reference material.

In another embodiment of the present invention, there is provided an apparatus for measuring corrosion in an environment, comprising interleaved combs of dissimilar conducting materials deposited on a non-conducting surface, such as a glass surface.

In yet another embodiment of the present invention, there is provided a method of measuring corrosion in an environment by exposing the apparatus to the environment and measuring the current and potential characteristics of the apparatus, wherein the measurement indicates electrochemical activity and thus the corrosion occurring.

The following examples are given for the purpose of illustrating various embodiments of the invention and are not meant to limit the present invention in any fashion.

EXAMPLE 1
The Prototype of Vapor Corrosion Cell 1

Vapor corrosion cell is a device for the measurement of corrosion of conductive materials in atmospheres containing chemically reactive gases and water vapor. The device consists of a series of strips of alternating dissimilar conducting materials 3 and 4, usually metals or alloys, separated by a thin strip of non-conducting material 5 in a sandwich structure. All of the strips of each similar conducting material are electrically connected (FIG. 1). The edges of the strips are exposed to atmospheres containing water vapor and a reactive vapor or gas. Under these conditions, an electrochemical potential is developed between the dissimilar metals and if the electrical circuit is closed, a current flows. Measurement of this current or potential provides an indication of the electrochemical activity and thus the corrosion occurring at the exposed surfaces.

EXAMPLE 2
Working Principle of Vapor Corrosion Cell

The device is based on the principle that most materials will adsorb a thin layer of water from the atmosphere if the relative humidity is high. If reactive vapors, such as carbon dioxide, nitrogen dioxide, sulfur dioxide, hydrogen halides, ammonia or other materials are present, they will react with the adsorbed water resulting in an ionic solution. The thin film of adsorbed solution now becomes conducting. The non-conducting separating film is selected to be thin enough so that the adsorbed solution layer can bridge the gap between the dissimilar metals, and an electrochemical cell results. The current and potential characteristics of the cell are dependent on the following factors: 1) pressure of reactive vapors in the atmosphere (in equilibrium with dissolved reacted vapor); 2) water vapor concentration in the atmosphere; 3) nature and surface area of the two dissimilar conductors; 4) nature and thickness of the separating non-conductor material and 5) the ambient temperature. By controlling all but one of these parameters, the remaining parameter may be measured.

For example, the present invention envisions a cell composed of several (4 to 10) strips of aluminum, separated from an equal number of strips of titanium by a 0.025 mm thick strip of polymer film (i.e., polyethylene or other polymer) in the manner shown in FIG. 1. On exposure to an atmosphere of dry nitrogen, no measurable current flows between the aluminum and the titanium. On exposure to an atmosphere containing water vapor and nitrogen dioxide, a current flows, proportional to the nitrogen dioxide content of the atmosphere. By fixing the atmospheric composition and changing the aluminum strips to magnesium strips, for example, the current that flows is an indication of the corrosion of magnesium. Comparison to the current from the aluminum/titanium couple provides an indication of the reactive corrosion behavior of aluminum and magnesium, both referenced to titanium.

EXAMPLE 3
Applications of Vapor Corrosion Cell 1

Some examples (not exhaustive) of how this device could be used include measuring air pollutants such as nitrogen oxides and sulfur oxides; measuring the corrositivity of polluted atmospheres toward exposed metal structures and providing materials selection criteria based on corrosion resistance. It can be used with metals or alloys which cannot be deposited in a thin film (i.e., stainless steel). A person having ordinary skill in this art would readily recognize other and different uses of the device of the present invention.

EXAMPLE 4
The Prototype of Vapor Corrosion Cell 2

Figure 2:
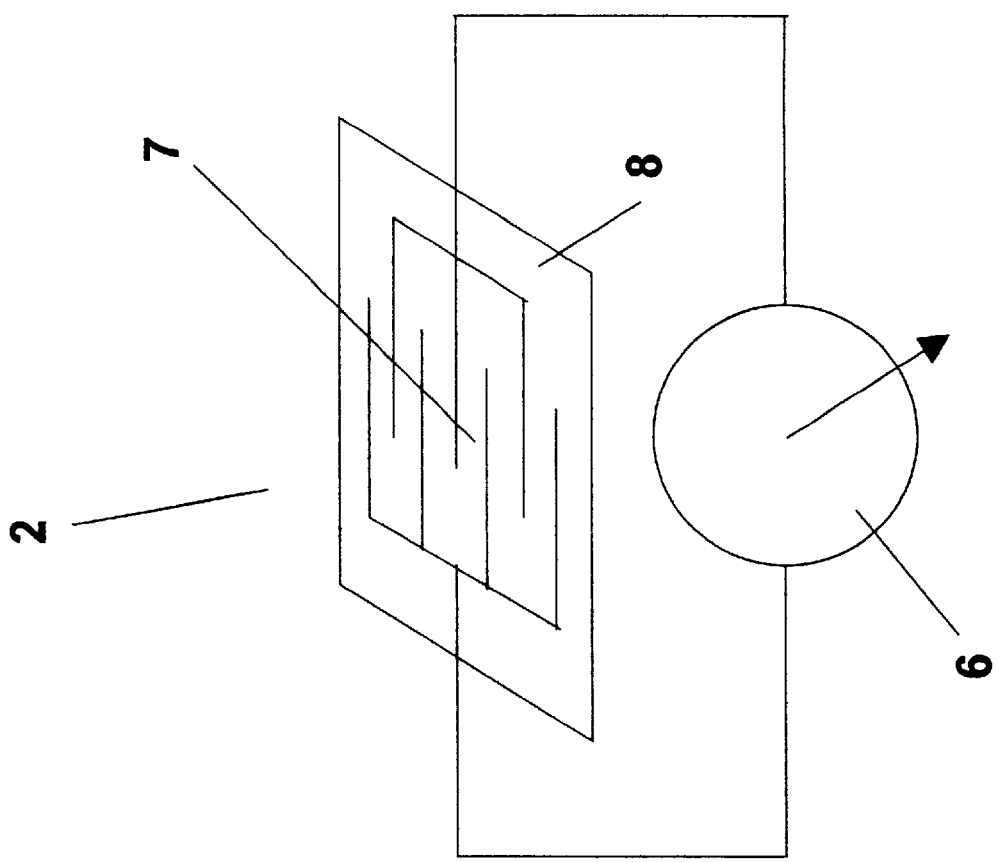
FIG. 2 shows the prototype of vapor corrosion cell 2 comprising interleaved combs 7 deposited on a non-conducting surface 8, wherein the interleaved combs 7 contain strips made of a sacrificial metal material and strips made of a reference metal material. The cell is molded into a compact block and further connected to a current measuring/recording device 6, such as an ammeter.

A cell based on the same concepts could be constructed by deposition of interleaved combs of dissimilar metals 7 on a non-conducting surface 8 (i.e., aluminum and gold vapor deposited on glass) (FIG. 2). This device, having advantages in construction and reproducibility, would work well for measuring air pollutants and the corrositivity of polluted atmospheres toward exposed metal structures.

EXAMPLE 5
Determination of Relative Corrosion Resistance of Alloys

Expose a vapor corrosion cell containing alternating strips of aluminum (zinc, magnesium, or other active sacrificial material) and strips of copper (titanium, stainless steel or other reference material) to a humid, corrosive atmosphere, and measure the resulting current I'. Expose a vapor corrosion cell containing alternating strips of aluminum (or zinc) and strips of a test alloy or metal to the same humid, corrosive atmosphere, and measure the resulting current I. The metal strips have same surface areas in both settings. I/I' is defined as the relative corrosion rate of the test alloy to copper (or other reference material) under the above mentioned conditions.

EXAMPLE 6
Prototype Testing

Initial testing shows that the vapor corrosion cell is very sensitive to corrosion. In addition, the process is reversible and the cell can be utilized to give multiple measurements.

Figure 3:
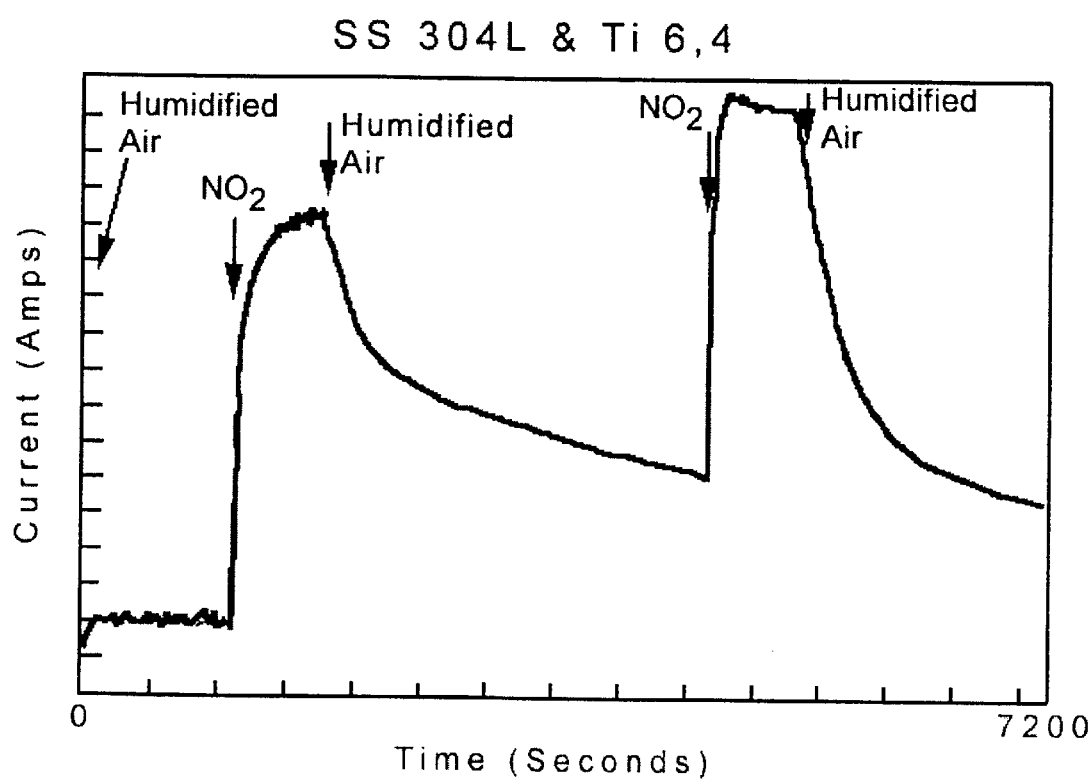
FIG. 3 shows a corrosion measuring process using a vapor corrosion cell.

FIG. 3 shows the data obtained in a typical corrosion measurement process. A vapor corrosion cell constructed of five strips of a titanium alloy (Ti-6Al-4V) as a reference material, five strips of 304L stainless steel as a sacrificial metal and separated by 0.025 mm thick polyethylene insulator strips was exposed to humid air at constant temperature at the time mark of 0 sec. At the time mark of approximately, 1000 sec, nitrogen dioxide gas at a concentration of approximately 500 parts per million was added to the environment. The addition of the chemically reactive gas caused the ammeter to register an increase in current flow indicative of corrosion of the sacrificial material. At the time mark of approximately 2000 sec the nitrogen dioxide was removed from the environment by displacement with humidified air and the ammeter registered a smaller electrochemical current. The cycle was repeated during the period 4500 to 6000 sec as shown in FIG. 3. The difference in current flow can be measured and related to the pressure of the reactive vapor, the humidity of the environment, the nature and surface area of the two dissimilar conductors, the nature and thickness of the separating non-conductor, and the ambient temperature.

SUMMARY

The present invention is directed to a vapor corrosion cell for sensing and evaluating the corrosive effects of atmospheric and chemical substances. The cell employs molecular adsorbed layers as electrolytes, which comes directly from the atmosphere. This apparatus can be used for real-time measurement and can be made compact. For example, the dimension of the cell can be as small as 50 mm×50 mm×10 mm (length×width×depth). However, the effectiveness of the cell depends upon water concentration in the atmosphere, which is uncontrollable. In addition, calibration is needed before use.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An apparatus for measuring corrosion in a gaseous environment containing chemically reactive gases or water vapor, said apparatus comprising:

a sensor, in the form of a sandwich structure, the sensor comprising:
   a plurality of strips of a first conducting material ($M_1$), alternated by a series of strips of a second conducting material ($M_2$), wherein said strips of the first conducting material ($M_1$) and said strips of the second conducting material ($M_2$) are electrically connected and said materials are dissimilar: and
   a plurality of thin strips of a non-conducting material, wherein said strips of non-conducting material separate said series of strips of said first conducting material ($M_1$) from said strips of said second conducting material ($M_2$) to form said sandwich structure, wherein said strips of non-conductive material are sufficiently thin, having thicknesses of about 0.01 to about 0.05 mm, such that that they comprise means for reacting with humidity in said reactive gaseous environment to form thin films of absorbed, solution the thin films of adsorbed solution bridging the gaps between the plurality of strips of the first conducting material and the plurality of strips of the second conducting material.

2. The apparatus of claim 1, comprising means for reacting with an environment in which said chemically reactive gas is selected from the group consisting of carbon dioxide, nitrogen dioxide, sulfur dioxide, hydrogen halides, ammonia, hydrogen sulfide and nitrogen-containing acids.

3. The apparatus of claim 1, wherein the number of said strips of the first conducting material ($M_1$) is from 4 to 10.

4. The apparatus of claim 1, wherein the number of said strips of the second conducting material ($M_2$) is from 4 to 10.

5. The apparatus of claim 1, wherein said apparatus is further connected to a current measuring/recording device.

6. The apparatus of claim 5, wherein said current measuring/recording device is an ammeter.

7. The apparatus of claim 5, wherein said apparatus provides real-time and quantitative corrosion measuring.

8. The apparatus of claim 1, wherein each of said conducting materials is selected from the group consisting of a metal and an alloy.

9. The apparatus of claim 1, wherein said first conducting material ($M_1$) is an active sacrificial material selected from the group consisting of aluminum, zinc, magnesium and an alloy, wherein said alloy is a mixture of two or more of the metals selected from the group consisting of aluminum, zinc and magnesium.

10. The apparatus of claim 1, wherein said second conducting material ($M_2$) is a reference material selected from the group consisting of titanium, copper, stainless steel, gold and platinum.

11. The apparatus of claim 1, wherein said apparatus has a length of about 50 mm, a width of about 50 mm, and a depth of about 10 mm.

12. A method of measuring corrosion in a gaseous environment, comprising the steps of:

exposing the apparatus of claim 1 to said environment;

measuring current flowing between the strips of the first conducting material and the strips of the second conducting material, wherein the measurement of the current indicates electrochemical activity and the extent of corrosion.

13. The method of claim 12, wherein said environment contains chemically reactive gases or water vapor.

* * * * *